US007967746B2

(12) United States Patent
Leroy et al.

(10) Patent No.: US 7,967,746 B2
(45) Date of Patent: Jun. 28, 2011

(54) RECTOSCOPE HAVING LIGHT-EMITTING ELEMENTS

(75) Inventors: Joel Jules Louis Leroy, Bully les Mines (FR); Jacques Francois Bernard Marescaux, Scharrachbergheim (FR); Didier Raoul Daniel Mutter, Vendenheim (FR); Michel Joseph Emile Vix, Niederhausbergen (FR)

(73) Assignee: Karl Storz GmbH & Co. KG (DE)

( * ) Notice: Subject to any disclaimer, the term of this patent is extended or adjusted under 35 U.S.C. 154(b) by 868 days.

(21) Appl. No.: 11/550,203

(22) Filed: Oct. 17, 2006

(65) Prior Publication Data
US 2007/0093692 A1      Apr. 26, 2007

(30) Foreign Application Priority Data
Oct. 17, 2005   (DE) .......................... 10 2005 050 554

(51) Int. Cl.
*A61B 1/06* (2006.01)
(52) U.S. Cl. ........................ 600/182; 600/178; 362/574
(58) Field of Classification Search .................. 600/182, 600/129, 178; 362/574
See application file for complete search history.

(56) References Cited

U.S. PATENT DOCUMENTS

| 3,146,775 | A | | 9/1964 | Moore et al. .................. 600/200 |
| 3,261,349 | A | | 7/1966 | Wallace ........................ 600/135 |
| 3,581,738 | A | | 6/1971 | Moore .......................... 524/842 |
| 3,945,371 | A | | 3/1976 | Adelman ...................... 600/121 |
| 4,207,874 | A | * | 6/1980 | Choy ............................ 600/108 |
| 4,306,546 | A | | 12/1981 | Heine et al. ...................... 128/6 |
| 4,732,448 | A | * | 3/1988 | Goldenberg ................... 385/33 |
| 4,736,733 | A | * | 4/1988 | Adair ............................ 600/109 |
| 5,402,768 | A | * | 4/1995 | Adair ............................ 600/106 |
| 5,456,245 | A | * | 10/1995 | Bornhop et al. .............. 600/139 |
| 6,063,024 | A | * | 5/2000 | Yamamoto .................... 600/160 |

(Continued)

FOREIGN PATENT DOCUMENTS
DE      1 248 222        8/1967
(Continued)

OTHER PUBLICATIONS

European Search Report, Feb. 22, 2007, 5 pages.

*Primary Examiner* — John P Leubecker
*Assistant Examiner* — Jeffrey H Chang
(74) *Attorney, Agent, or Firm* — St. Onge Steward Johnston & Reens LLC

(57) ABSTRACT

A rectoscope has a tube and a handle protruding therefrom. A number of light-emitting elements are arranged circumferentially distributed at the distal end of the tube. The tube includes an inner pipe, an outer pipe and an annular body at the distal ends of the inner and outer pipe. The annular body includes an end ring provided with bores for receiving the light-emitting elements. The annular body also includes an annular flange extending away proximally and having an outside diameter corresponding to a clear inside diameter of the outer pipe. The end ring has an outside diameter corresponding approximately to an outside diameter of the outer pipe.

11 Claims, 5 Drawing Sheets

U.S. PATENT DOCUMENTS

| | | | |
|---|---|---|---|
| 6,428,473 B1 * | 8/2002 | Leonard et al. | 600/219 |
| 6,497,654 B1 | 12/2002 | Leonard et al. | 600/245 |
| 6,679,838 B2 * | 1/2004 | Bala | 600/178 |
| 2002/0007111 A1 * | 1/2002 | Deckert et al. | 600/177 |
| 2002/0013601 A1 | 1/2002 | Nobles et al. | 606/193 |
| 2003/0100819 A1 | 5/2003 | Newman et al. | 600/300 |
| 2003/0163030 A1 * | 8/2003 | Arriaga | 600/182 |

FOREIGN PATENT DOCUMENTS

| | | |
|---|---|---|
| DE | 1 956 345 | 5/1970 |
| DE | 2 326 786 | 12/1973 |
| GB | 1134972 | 11/1968 |
| RU | 2215462 C2 * | 11/2003 |

* cited by examiner

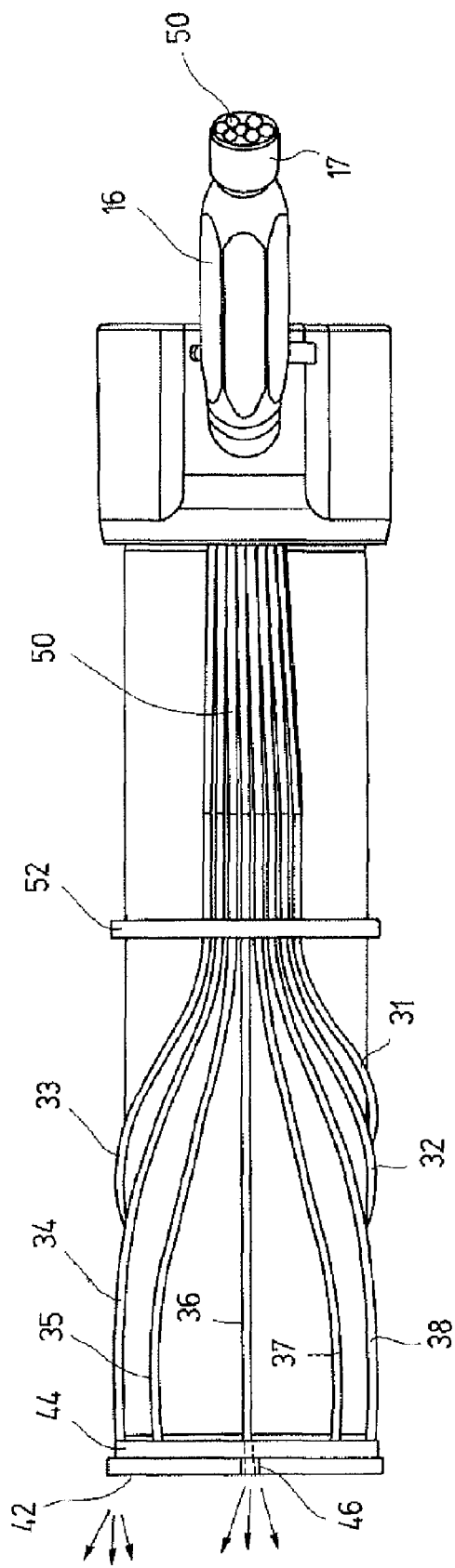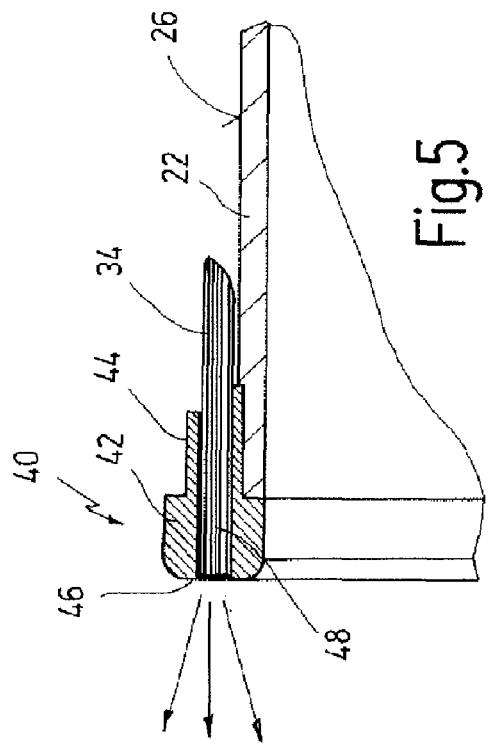
Fig.4
Fig.5

RECTOSCOPE HAVING LIGHT-EMITTING ELEMENTS

BACKGROUND OF THE INVENTION

The invention relates to a rectoscope having a tube and a handle protruding therefrom.

The tube in the form of a pipe open at both ends has, for example, a length of 20 cm and a diameter of approximately 40 mm. For transanal rectal surgery, the tube is introduced into the rectum, and instruments for carrying out operational procedures can be guided in or through via the tube.

Rectoscopes are also used for a so-called end-to-end anastomosis. In this operation, a segment of intestines, which are, for example tumorous, is removed and the two ends of the intestines resulting therefrom are rejoined to one another with the aid of a so-called stapler. Further operating instruments are introduced during this operation via an access in the abdominal cavity. These are, firstly, optics for illuminating and observing the operating site and, secondly, forceps and scissors for removing the defective section of intestines. Furthermore, a counter-pressure plate is introduced laparoscopically. This counter-pressure plate is required so that the stapler can join the two ends of the intestines to one another.

If hemorrhoids are being treated, a so-called hemorrhoid legator circular stapler is guided through the tube and can be used to place staples in order, for example, to clamp internal hemorrhoids.

The illumination of the operating site is performed entirely laparoscopically via optics introduced into the abdominal cavity, while the tube or the rectoscope itself has no illumination or luminous means.

The rectum is a relatively spacious operating site which requires well illuminated visual monitoring by the operator in order to handle the diverse instruments reliably.

It is an object of the invention to facilitate the handling of a rectoscope.

SUMMARY OF THE INVENTION

According to the invention, the object is achieved by virtue of the fact that a number of light-emitting elements are arranged in a circumferentially distributed fashion at the distal end of the tube of the rectoscope.

This has the advantage that a light source is available which emits from the tube at the distal end.

This greatly facilitates the handling of the rectoscope for the operator.

A light-emitting distal end is helpful as early as when introducing the tube into the rectum through the wide open anus.

In order to introduce the tube, it is customary firstly to push a conical spreader into the anus in order to spread the sphincter. The tube is then pushed into the rectum over this spreader inserted in the anus. The outside diameter of the spreader inserted in the anus corresponds to the clear inside diameter of the tube. The spreader completely fills the inner hollow space of the tube. The light-emitting elements facilitate the correct placement of the distal end of the tube onto the spreader, since the operator has a better view into this location.

After the withdrawal of the spreader, the tube is closed via an obturator and pushed several centimetres further into the rectum.

After the obturator has been removed from the rectoscope, the so-called stapler is introduced into the rectoscope. In this process, the stapler projects beyond the distal end of the rectoscope to a certain extent which is known to the operator, for example two centimetres. Because of the inventive illumination at the distal end of the rectoscope, the position of the stapler can be determined exactly with the aid of the optics, which have been brought to the operating site laparoscopically via the abdominal cavity. Since, as previously mentioned, it is known how far the distal end of the stapler protrudes from the distal end of the rectoscope, this position can be determined relatively exactly. The distal illumination at the rectoscope further helps to illuminate the operating site more effectively.

In a further refinement of the invention, an annular body in which the light-emitting elements are housed is arranged at the distal end of the tube.

This measure has the advantage that the light-emitting elements can be embedded in the annular body, and thus no bulky parts project.

In a further refinement of the invention, the light-emitting elements are the distal ends of light guides.

This measure has the advantage that light with a high light yield can be guided to the distal end of the tube via such light guides. The individual light guides can, for example, be designed as bundled glass fibres provided with a protective cover.

In a further refinement of the invention, the light guides are guided in the wall of the tube from the proximal to the distal end of the tube.

This measure has the advantage that the very slimly constructed components are integrated in the wall, and neither the outside of the tube, which is directly connected to the rectum, nor the inside, which is freely available for the through guidance of the numerous further operating instruments, is affected.

In a further refinement of the invention, the light guides are guided through the handle to a terminal light guide connection.

This measure has the advantage that the light guides can be guided in a space saving fashion to the light guide connection via which they are supplied with light from an external light source.

In a further refinement of the invention, the tube has an outer pipe and an inner pipe between which the light guides are guided.

This measure has the advantage that the light guides are accommodated between these two pipes in a protective fashion.

In a further refinement of the invention, the light guides are designed as a number of strands.

This measure has the advantage that the individual strands can then be guided to the light-emitting locations arranged in a circumferentially distributed fashion, depending on the desired arrangement.

In a further refinement of the invention, the distal end regions of the individual strands are accommodated in the annular body at the distal end.

This measure has the advantage that the light-emitting locations are accommodated in the annular body in a fixed and protected fashion. This also facilitates assembly. Thus, for example, it is possible in accordance with the arrangement to introduce into the annular body a number of bores into which the ends of the light guides are plugged.

In a further refinement of the invention, the strands are accommodated in the handle as a bundle.

This measure has the advantage of enabling compact guidance of the strands as a bundle through the handle.

In a further refinement of the invention, the strands are guided from proximal to distal as a bundle over a certain length of the tube and are fanned out in the distal end region of the tube to form the individual circumferentially distributed strands.

This measure has the substantial advantage that the bundle occupies only a small space as seen circumferentially about the tube, and so it is possible in this region to provide lateral openings for guiding further instruments into or through the tube.

Not until the distal end region is the bundle fanned out to form the circumferentially distributed light-emitting locations.

In a further refinement of the invention, the light guides are guided on the outside of the inner pipe and are held there by holding elements.

This greatly facilitates assembly and cleaning and contributes to holding the light guides in a permanently fixed fashion.

The inner tube with the light guides attached to its outside can be designed as a first module component which, after the inner tube has been fitted with the light guides and, if appropriate, the light intensity has also been checked, can be pushed into the outer tube, in which case there is now a need only to thread the bundle through the handle.

In a further refinement of the invention, the light-emitting elements are designed as light-emitting diodes.

This measure has the advantage that it is easy in terms of production engineering to insert in the ring at the proximal end light-emitting diodes which can then be mounted as a complete unit it is then further necessary merely to provide the supply of electric energy.

To this end, it is provided in a further refinement that the power cable for supplying the light-emitting diodes with energy is guided from proximal to distal in the wall of the tube.

It is possible in principle to proceed here again as in the case of the light guides, that is to say to carry out bundling and elegant guidance through the handle.

It goes without saying that the features mentioned above, and those still to be explained below, can be used not only in the respectively specified combination but also in other combinations or on their own without departing from the scope of the present invention.

BRIEF DESCRIPTION OF THE DRAWINGS

The invention is described and explained in more detail below with the aid of a selected exemplary embodiment in conjunction with the attached drawings, in which:

FIG. 4 shows a bottom view of the inner pipe, the outer pipe being omitted in the region thereof and—at the right hand end—the proximal end section of the outer pipe with handle protruding therefrom;

FIG. 5 shows a section in the region of the end at upper left in the illustration in FIG. 4 for the purpose of explaining the design of the annular body and of a light guide fastened therein.

DETAILED DESCRIPTION OF PREFERRED EMBODIMENTS

Figure 1:
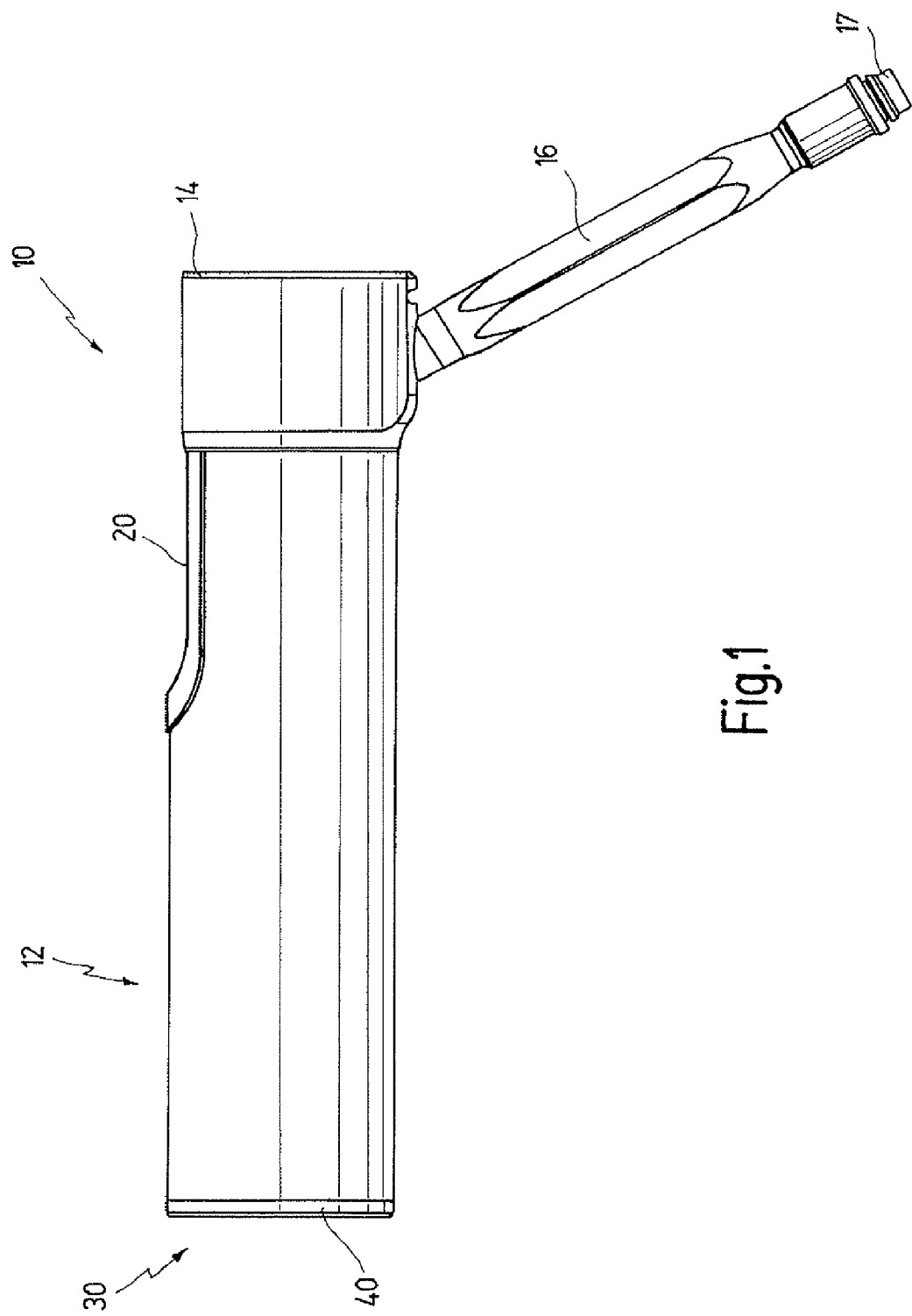
FIG. 1 shows a side view of a rectoscope according to the invention.

A rectoscope illustrated in FIGS. 1 to 5 is denoted in its entirety by the reference numeral 10.

As may be seen, in particular, from FIG. 1, the rectoscope 10 has a hollow cylindrical tube 12 which is open at both ends and from whose proximal end 14 a handle 16 stretches away laterally in a fashion protruding obliquely. The tube 12 is illustrated rectilinearly, but it can also run in a curved fashion.

Figure 2:
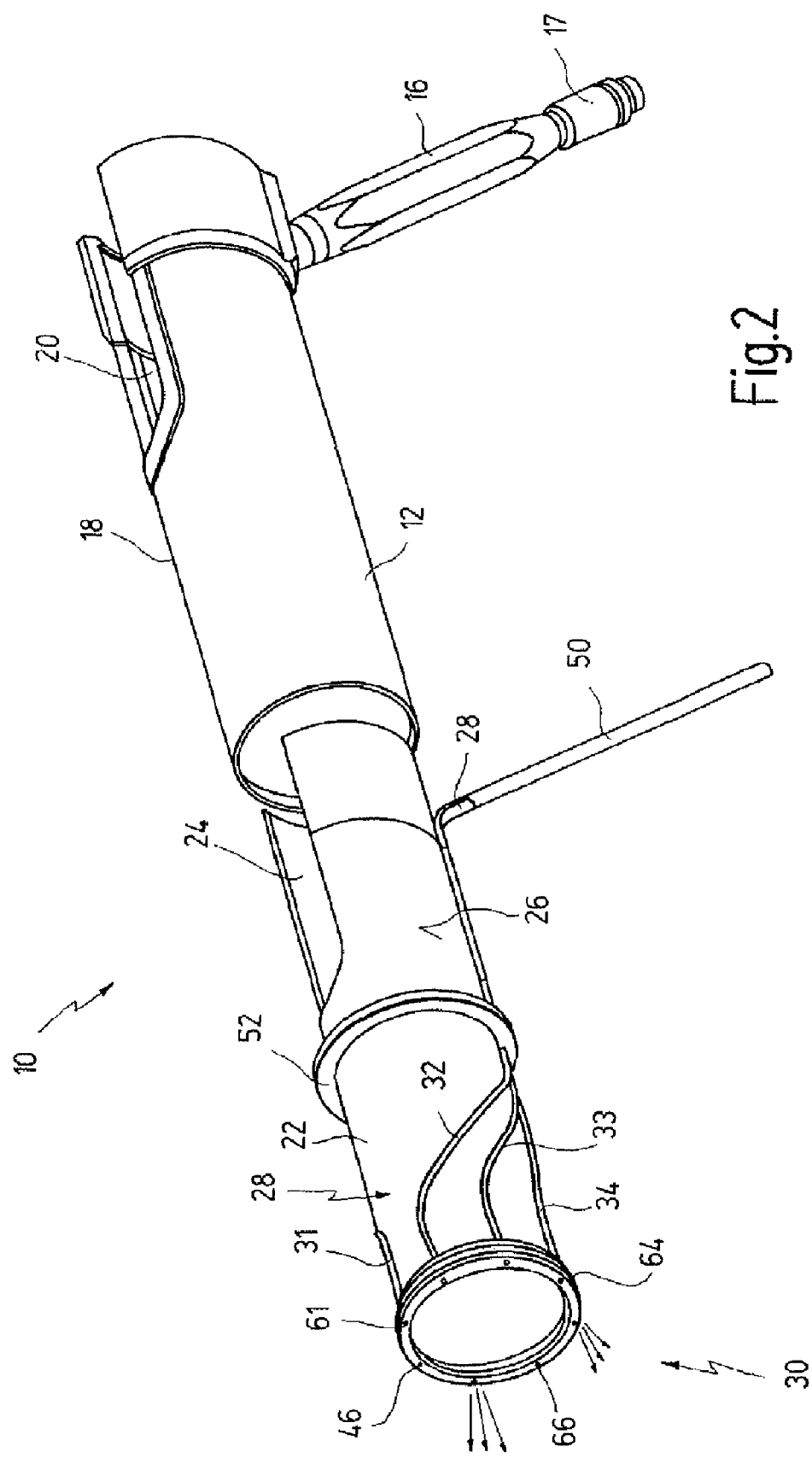
FIG. 2 shows an exploded illustration of the rectoscope with the inner pipe, withdrawn from the outer pipe, with the light guides.

It is to be seen from the exploded illustration of FIG. 2 that the tube 12 is composed of an outer pipe 18 and an inner pipe 22.

The outer pipe 18 has the abovementioned protruding handle 16 on its outside.

The length of the tube 12 in the illustrated exemplary embodiment is approximately 16 cm, and the clear inside diameter is approximately 35 mm.

A slot 20 is cut out of the outer pipe 18 opposite the handle 16.

The inner pipe 22 has approximately the same length, but its diameter is somewhat smaller, specifically by 2 to 3 mm, and a corresponding slot 24 is likewise provided in the inner pipe 22.

Light guides 28 are fitted on the outside 26 of the inner pipe 22.

The light guides 28 consist of eight strands 31 to 38.

Each strand consists of an outer jacket, be it of metal or plastic, in which numerous individual glass fibres are accommodated as actual light guiding bodies.

An annular body 40 is arranged on the inner pipe 22 at the distal end 30 of the inner pipe 22, which also simultaneously constitutes the distal end of the tube 12.

The annular body 40 is composed of an end ring 42 from which an annular flange 44 extends away proximally over a few millimetres (see FIG. 5, in particular).

The outside diameter of the end ring 42 corresponds approximately to the outside diameter of the outer pipe 18.

The outside diameter of the annular flange 44 corresponds to the clear inside diameter of the outer pipe 18. The inside of the annular flange 44 runs approximately at a spacing from the outside 26 of the inner pipe 22.

Eight bores 46 are introduced in the end ring 42 in a uniformly circumferentially distributed fashion, the distal end 48 of one of the strands 31 and 38 respectively being pushed into these eight bores 46. In this case, the distal end 48 is guided through below the annular flange 44 and between the outside 26 of the inner pipe 22.

Figure 3:
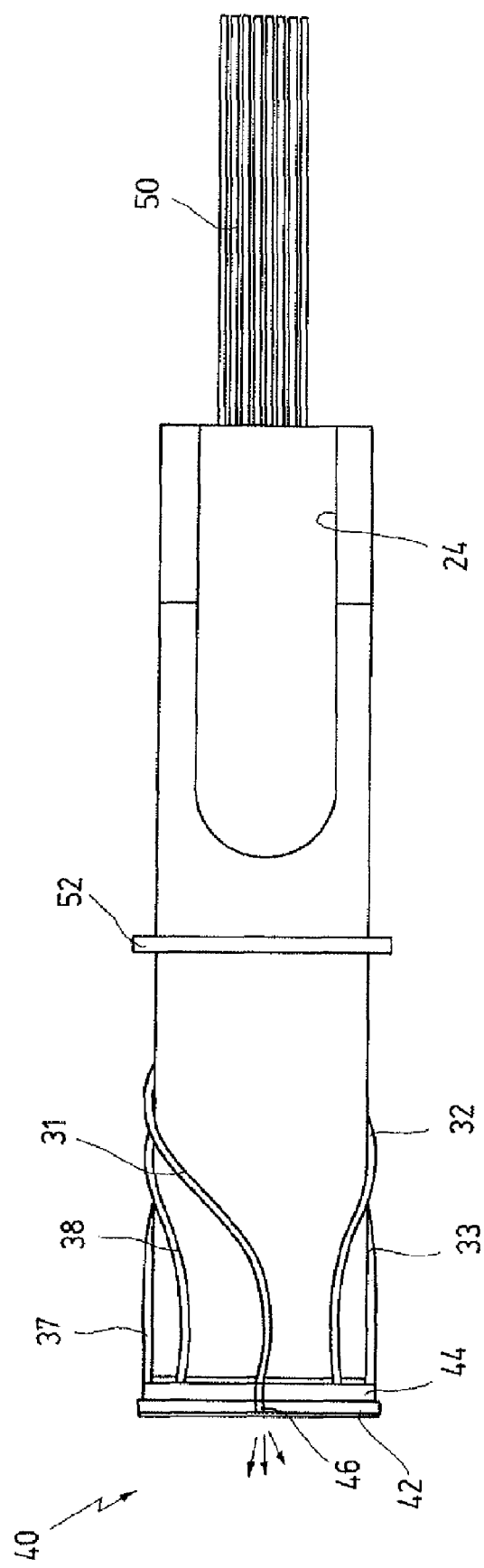
FIG. 3 shows a top view of the inner pipe of FIG. 2.

This gives rise to the distribution pattern of the strands 31 to 38 which may be seen from FIGS. 2, 3 and 4.

The eight strands 31 and 38 are combined to form a bundle 50, the bundle 50 being guided through the interior of the handle 16 up to a light guide connection 17 arranged on the outside thereof.

In the exploded illustration of FIG. 2, the bundle 50 is illustrated in a fashion angled away in order to show how it is accommodated in the handle 16 in the mounted state.

Initially, the alignment of the bundle 50 is as illustrated in FIG. 3 so that it can be pushed into the outer pipe 18.

Present in the outer pipe 18 in the region of the handle 16 is an opening via which the bundle 50 can be inserted into the handle 16. This is even further facilitated during mounting by two slots 20 and 24.

In the finally mounted state, thus, the bundle 50 composed of the eight strands 31 to 38 and coming from the handle 16 is guided further as bundle 50 over a certain extent of the length of the inner pipe 22 and is additionally held by an annular holding element 52. Subsequently, the bundle 50 fans out so that then the eight strands 31 and 38 are guided to the corresponding eight bores 46 in the end ring 42.

If the handle 16 is connected to a light source in the finally mounted state, the light is guided via the light guide 28 through the handle and up to the distal end 30.

The light is emitted there in punctiform fashion at the eight distal ends 48.

These eight emission points form light-emitting elements arranged in a circumferentially distributed fashion; here, it is only the elements 61, 64 and 66 which are denoted in FIG. 2.

The design described in FIGS. 1 to 4 constitutes, as it were, the basic body of a rectoscope 10.

Manipulations can then be carried out through the cavity of the tube 12 during handling, for example appropriate instruments can be pushed through in order to be able to undertake surgical procedures on the inside of the rectum.

For example, these can be operations on the hemorrhoids, also a tumourous section of the rectum.

The two remaining end pieces must be rejoined by a so-called end-to-end anastomosis. A so-called stapler is introduced in this case into the tube. All further instruments are brought to the operating site through the abdominal cavity.

Figure 6:
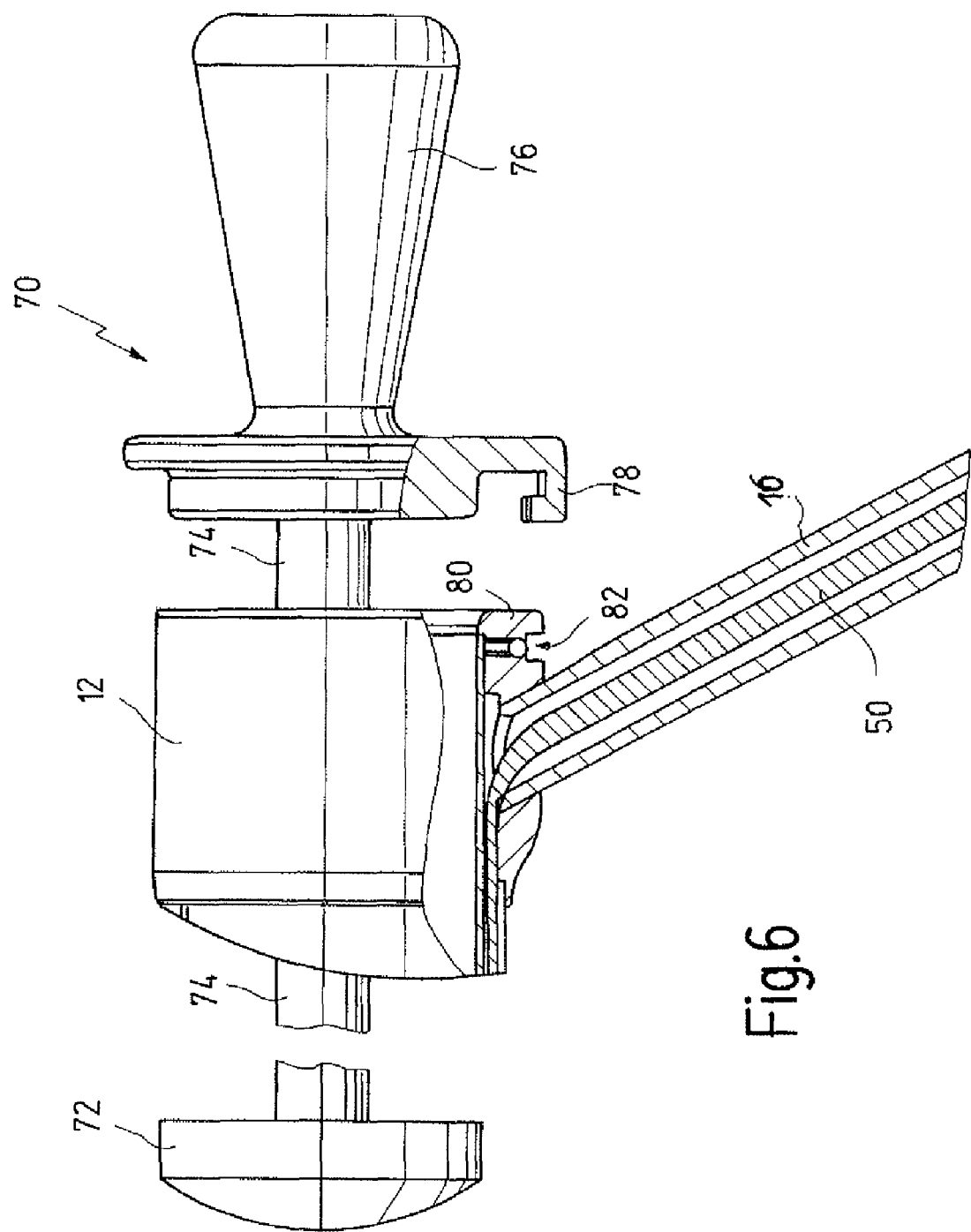
FIG. 6 shows a partially sectioned detailed illustration of the rectoscope of FIG. 1, an obturator just being pushed in in order to close the tube.

FIG. 6 illustrates precisely how a so-called obturator 70 is introduced into the tube 12 from the proximal end.

The obturator 70 has a stopper 72 at the distal end in order to close the distal end of the open tube 12. The stopper is connected via a rod 74 to a grip 76. The latter has a latching hook 78 which can latch with a corresponding spherical latch 80 at the proximal end region. A spring loaded ball 82 provides the holding force.

The tube 12 is closed at both ends when the obturator 70 is thus mounted and latched.

The rectoscope 10 is, for example, handled as follows:

A spreader which tapers conically at the distal end is firstly introduced into the anus of a patient in order to widen the anus. The outside diameter of the spreader corresponds approximately to the clear inside diameter of the tube 12.

Subsequently, the tube 12 is pushed over the spreader inserted in the anus and introduced a little into the rectum thereby. After the tube 12 has been pushed over the spreader, the spreader is withdrawn proximally through the tube 12.

The obturator 70 is now introduced and latched such that the tube 12 is tightly closed at both ends.

In this state, the tube 12 is now driven as far as desired into the rectum.

Subsequently, the obturator 70 is removed, and the desired instruments, for example a stapler, can be guided through the tube 12. The distal illumination at the rectoscope facilitates the determination of the position of the stapler and further serves to illuminate the operating site more effectively.

In the case of instruments with electrically operated tools, for example blades or suturing devices, these instruments must be supplied with electricity by cable.

Since staplers are usually of curved design, the proximal end region can project over the slots 20, 24.

Owing to the smooth linear guidance of the tube, that is to say there is no obstruction of the inside of the inner pipe 22 by any sort of components, the instruments can be mounted in a fashion sealed off from the outside, this being additionally promoted by the geometry of the annular body 40, which can serve as bearing body or bearing flange for such tools at the distal end.

After carrying out the surgical procedures, the rectoscope 10 is withdrawn from the rectum. Depending on the configuration of the connection between inner pipe 22 and outer pipe 18, the instruments can detach from one another for cleaning purposes and be cleaned and sterilized.

When these instruments are made from high quality materials, for example stainless steel, it is also possible for them to be interconnected in a sealing fashion, for example by soldering, such that they need not be taken apart for cleaning.

It is also possible for such rectoscopes to be designed for being used once such that cost effective plastics materials can then be used.

Combinations are also possible. Thus, for example, the outer pipe 18 and handle 16 can consist of steel, while the inner pipe 22 together with light guide 22 mounted thereon can be produced from plastics materials.

It was previously stated that the light guides 28 constitute glass fibres as light guiding and light emitting elements.

It is also possible to insert in the bores 46 present in the annular body 40 light emitting diodes which then are supplied with current via appropriate power cables. These power cables can then be guided in like manner as the strands 31 to 38, bundled and guided to a power connection at the end on the handle 16.

What is claimed is:

1. A rectoscope, having a hollow tube and a handle protruding therefrom, wherein a number of light-emitting elements are arranged in a circumferentially distributed fashion at a distal end of said tube, said tube having an outer pipe and an inner pipe, each of said pipes having a distal end, wherein energy guides of said light-emitting elements are guided between said pipes to said distal ends thereof, an annular body is arranged at said distal ends of said inner and said outer pipe, said annular body having an end ring provided with bores for receiving at least a distal end section of said light-emitting elements, said end ring being the very end of the rectoscope at the distal end, and wherein said bores are designed as circumferentially closed axial throughbores in said end ring, and said annular body having an annular flange extending away proximally, said annular flange having an outside diameter corresponding to a clear inside diameter of said outer pipe, and said end ring having an outside diameter corresponding approximately to an outside diameter of said outer pipe.

2. The rectoscope of claim 1, wherein said energy guides are light guides and said light-emitting elements are distal ends of said light guides.

3. The rectoscope of claim 2, wherein said light guides are guided in a wall of said tube from a proximal to a distal end of said tube.

4. The rectoscope of claim 3, wherein said light guides are guided through said handle to a terminal light guide connection.

5. The rectoscope of claim 2, wherein said light guides are designed as strands.

6. The rectoscope of claim 5, wherein a distal end region of said strands are accommodated in said annular body at said distal end of said tube.

7. The rectoscope of claim 6, wherein said strands are accommodated in said handle as a bundle.

8. The rectoscope of claim 5, wherein said strands are guided from proximal to distal over a certain length of said tube as a bundle which fans out in a distal end region of said tube to form individual, circumferentially distributed strands.

9. The endoscope of claim 2, wherein said light guides are guided on an outside of said inner pipe and are held there by at least one holding element.

10. The rectoscope of claim 1, wherein said light-emitting elements are designed as light-emitting diodes.

11. The rectoscope of claim 10, wherein said energy guides are power cables for supplying said light-emitting diodes with energy which are guided from proximal to distal in a wall of said tube.

* * * * *